United States Patent [19]
Negus et al.

[11] Patent Number: 5,836,939
[45] Date of Patent: *Nov. 17, 1998

[54] SURGICAL LASER HANDPIECE

[75] Inventors: Charles Christopher Negus, Taunton; Scott Andrew Morrell, Hopedale; Stephen J. Linhares, Taunton, all of Mass.

[73] Assignee: PLC Medical Systems, Inc., Milford, Mass.

[*] Notice: This patent issued on a continued prosecution application filed under 37 CFR 1.53(d), and is subject to the twenty year patent term provisions of 35 U.S.C. 154(a)(2).

[21] Appl. No.: 548,268

[22] Filed: Oct. 25, 1995

[51] Int. Cl.[6] ................................................. A61B 17/36
[52] U.S. Cl. ................................................. 606/11; 606/17
[58] Field of Search ................................. 606/14, 15, 16, 606/17, 19

[56] References Cited

U.S. PATENT DOCUMENTS

| | | | |
|---|---|---|---|
| 5,078,711 | 1/1992 | Kakami et al. | 606/16 |
| 5,163,935 | 11/1992 | Black et al. | 606/17 |
| 5,401,270 | 3/1995 | Muller et al. | 606/15 X |
| 5,403,308 | 4/1995 | Wood et al. | 606/17 |
| 5,469,524 | 11/1995 | Esch et al. | 606/15 X |
| 5,575,787 | 11/1996 | Abela et al. | 606/15 |
| 5,593,404 | 1/1997 | Costello et al. | 606/15 |
| 5,616,141 | 4/1997 | Cipolla | 606/15 |

*Primary Examiner*—John P. Lacyk
*Assistant Examiner*—Sonya Harris-Ogugua
*Attorney, Agent, or Firm*—Iandiorio & Teska

[57] ABSTRACT

A surgical laser handpiece comprising: an outer barrel having an inner chamber; an inner zoom barrel movable in said chamber relative to said outer barrel; at least a first lens device in said zoom barrel for propagating and focusing a laser beam; and a drive member externally accessible on said outer barrel for moving said zoom barrel with one hand relative to said outer barrel for varying the focus of the laser beam.

4 Claims, 3 Drawing Sheets

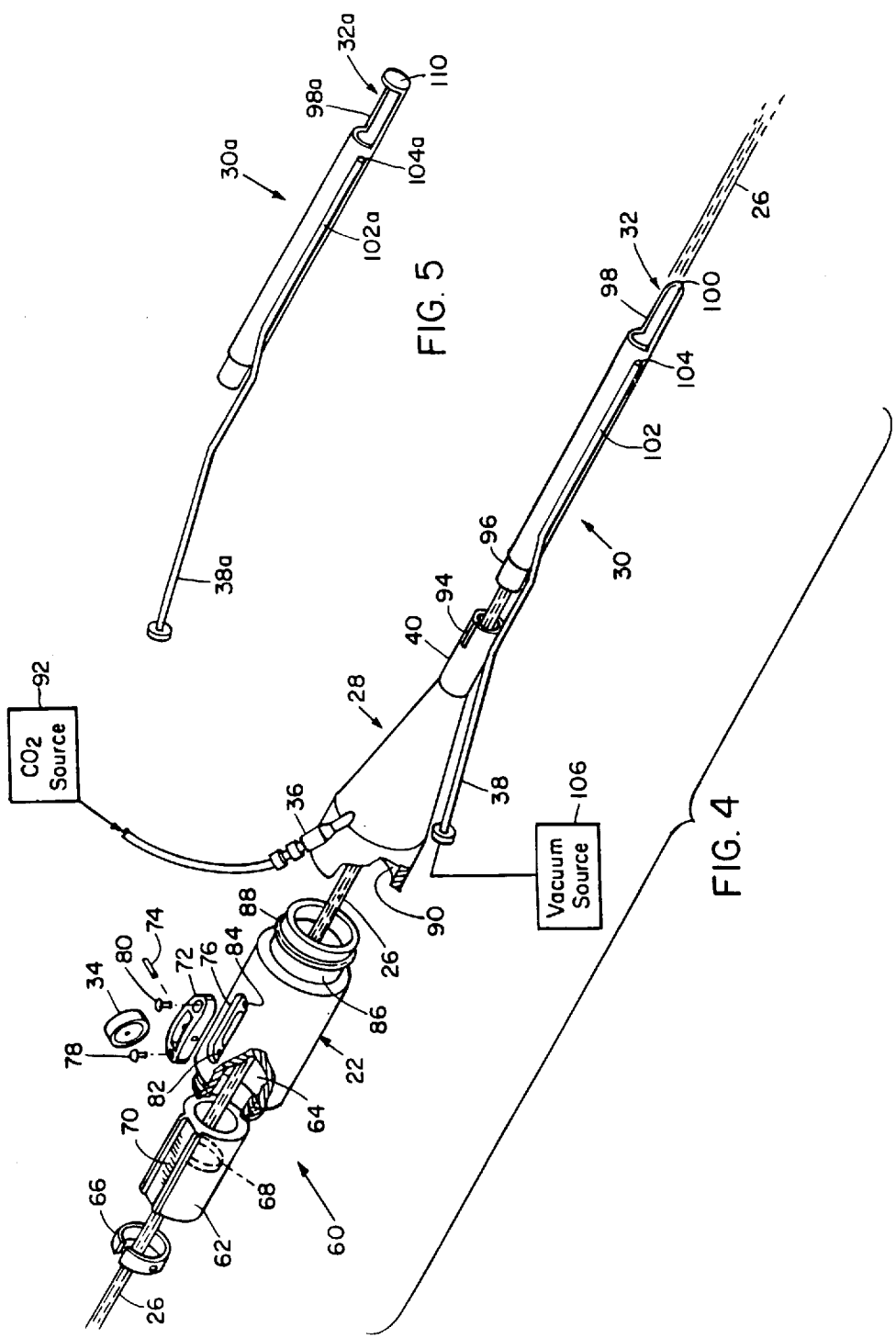

SURGICAL LASER HANDPIECE

FIELD OF INVENTION

This invention relates to an improved surgical laser handpiece.

BACKGROUND OF INVENTION

The human uvula sweeps the back of the throat when swallowing and creates a point of drainage for the nasal passages. When the uvula and/or palate become enlarged or the muscles become weak or relaxed a narrowing of the breathing passage occurs which can result in snoring. Enlargement due to fatty deposits can occur in people who are obese; loss of muscle tone can occur in people who consume large quantities of alcohol. Age and illness can also cause such conditions which contribute to snoring. Often the condition is so severe that surgical intervention is required to reshape the uvula and soft palate in a procedure called uvulapalatoplasty. This surgical procedure can remove a portion of the uvula and/or make trenches which cause the uvula muscles to contract and tighten up to the palate. Historically this surgical procedure was done as a full surgical operation with general anesthesia and multi-day hospital stay. Presently using lasers it can be done with or without local anesthesia on an outpatient basis. During the procedure the surgeon may choose to sharply focus the laser to make a sharp slicing cut or may de-focus the laser somewhat to cause more heating which engenders greater muscle constriction and faster coagulation.

However, the focus adjustment requires both the surgeon's hands to manipulate two counter-rotating barrels which effect the focus variation. A further complication arises because the surgeon must hold the patient's tongue out of the way with a tongue depressor. Thus any change in focus necessitates an interruption or delay in the surgical procedure.

Separately, the procedure produces much smoke and laser plume, typically cloudy and noxious, which obscures the surgeon's view and creates anxiety for the patient. The smoke is generally drawn away by an assistant with a smoke evacuator held close to the patient's mouth.

SUMMARY OF INVENTION

It is therefore an object of this invention to provide a surgical laser handpiece which provides for focus adjustment without interruption of the surgical procedure.

It is a further object of this invention to provide such a surgical laser handpiece which requires only one hand to adjust the focus.

It is a further object of this invention to provide such a surgical laser handpiece in which the smoke and laser plume are cleared at the surgical site thereby avoiding accumulation in the patient's mouth or other body cavity and avoiding obfuscation of the surgeon's view.

It is a further object of this invention to provide such a surgical laser handpiece in which the smoke and laser plume are cleared without the need for an assistant.

It is a further object of this invention to provide such a surgical laser handpiece which reduces patient anxiety.

The invention results from the realization that a truly improved and more effective surgical laser handpiece can be achieved which allows single-handed operation, a clear view of the surgical site, removes smoke and laser plume automatically and reduces patient anxiety by providing a lens device which is movable in the handpiece using only one hand and providing an evacuator conduit which extends to and removes smoke directly at the surgical site.

This invention features a surgical laser handpiece including an outer barrel having an inner chamber, an inner zoom barrel movable in the chamber relative to the outer barrel, at least a first lens device in the zoom barrel for propagating and focusing a laser beam, and a drive member externally accessible on the outer barrel for moving the zoom barrel with one hand relative to the outer barrel for varying the focus of the laser beam.

In a preferred embodiment there may be a second lens device mounted in the outer barrel optically aligned with the first lens device. The drive member may include a rotatable wheel mounted on the outer barrel and a friction drive surface on the zoom barrel engaged with the wheel. The drive member may include a slot in the outer barrel and a tab on the zoom barrel extending into the slot.

This invention also features a surgical laser handpiece including a tip assembly, a barrel section for supporting the tip assembly and having a lens device for propagating and focusing a laser beam at, near or beyond the tip of the tip assembly, and a smoke evacuator conduit extending along the tip assembly and terminating in an intake port proximate the tip and having an exhaust port connectable to a vacuum source for drawing out smoke and laser plume at the generation site. The tip may include a guide member for gauging the point of focus of the laser beam and a backstop on the guide member for preventing further propagation of the laser beam. There may also be a purge tube for introducing a purge gas into the barrel section to drive the smoke and plume away from the lens device toward the tip.

DISCLOSURE OF PREFERRED EMBODIMENT

Other objects, features and advantages will occur to those skilled in the art from the following description of a preferred embodiment and the accompanying drawings, in which:

FIG. 4 is an enlarged exploded view of the surgical laser handpiece according to this invention;

FIG. 5 is a similar view showing an alternative tip assembly;

Figure 1:
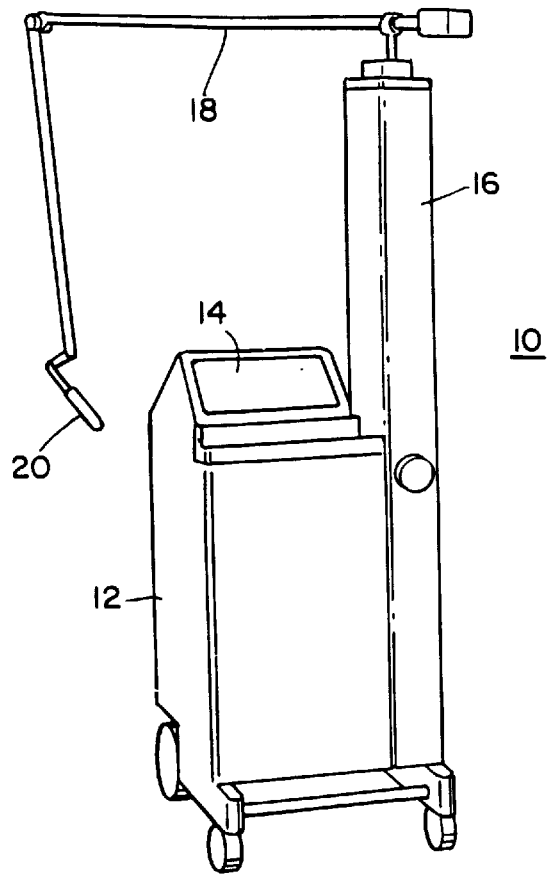
FIG. 1 is a three-dimensional view of a surgical laser system employing the handpiece of this invention.
Figure 2:
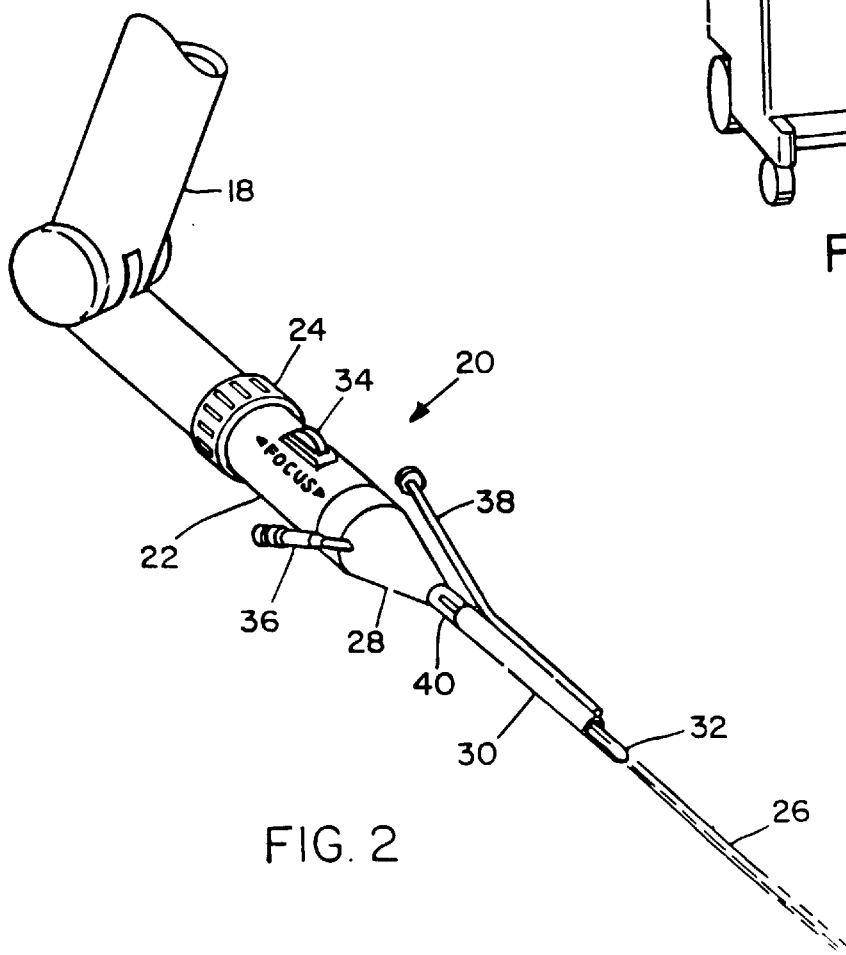
FIG. 2 is an enlarged detail view of the handpiece of this invention.

There is shown in FIG. 1 a surgical laser system 10 including a power supply and control circuits 12 which are operated by monitor and control display 14 to drive laser 16 which propagates a laser beam through articulated arm 18 and handpiece 20. Handpiece 20, FIG. 2, includes a barrel 22 connected to the end of arm 18 by a threaded knurled nut 24. The laser beam 26 is propagated through barrel 22 in conical section 28 and tip assembly 30. Typically laser beam 26 is focused at the tip 32 of tip assembly 30 by means of a focusing mechanism in barrel 22 which is operated by thumb wheel 34. A purge gas is introduced through purge tube 36 to drive smoke and laser plume away from barrel 22 and the optical elements toward tip 32. Exhaust tube 38 forms a part of tip assembly 30. Tip assembly 30 is slip-fit into the end 40 of conical section 28.

Figure 3:
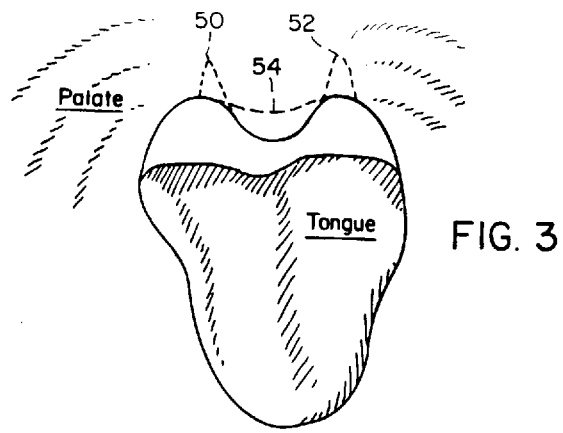
FIG. 3 is a schematic view of the throat of a patient showing the uvulapalatoplasty procedure.

In performing the uvulapalatoplasty, the surgeon typically aims the laser beam in order to create trenches 50, 52, FIG. 3, on either side of the uvula to cause the muscles to constrict and also may trim off a portion of the uvula itself, reshaping and reducing the size of the uvula to the shape of contour 54. During this procedure the surgeon may wish to sharply focus the laser beam in order to primarily cut or slice to create trenches 50, 52 and contour 54, or he may desire to defocus the laser beam somewhat so as to generate more heat in these cutting areas 50, 52 and 54, thereby causing greater muscle constriction and more coagulation.

Focusing mechanism 60, FIG. 4, includes an inner zoom barrel 62 that moves axially, in chamber 64 of outer barrel 22. Retainer ring 66 retains lens 68 inside of zoom barrel 62. Zoom barrel 62 includes a flat friction surface 70 which is engaged with the circumference of thumb wheel 34 to move zoom barrel 62 back and forth axially inside of chamber 64 relative to outer barrel 22. Thumb wheel 34 is mounted in wheel guide 72 by means of pin or axle 74 and the entire guide is mounted in slot 76 by screws 78, 80 which engage with threads in holes 82 and 84. Extension 86 of barrel 22 includes O-ring 88 for sealingly engaging with the inner bore 90 of conical section 28. Conical section 28 includes purge tube 36 which is connected to a source of purge gas 92 such as $CO_2$. The introduction of the purge gas through purge tube 36 drives any smoke or laser plume away from outer barrel 22 and the lens mechanism toward tip 32. The other end of conical section 28 includes a reduced portion 40 having a slot 94 to provide a slip fit with the proximal end 96 of tip assembly 30. At the tip 32 of tip assembly 30 is tip guide 98 which acts as a gauge to indicate the focal point of the laser beam which is typically at the very end 100 of tip guide 98. Carried on tip assembly 30 is smoke evacuator tube 102 whose exhaust port 104 is close to the tip 32 of tip assembly 30 in order to draw out the smoke and laser plume which is created by the laser striking the tissue. The other end 38 of smoke evacuation conduit 102 is attached to a vacuum source 106. In an alternative form, tip assembly 30a, FIG. 5, may include a back stop 110 at the end of tip guide 98a in order to prevent the laser beam from propagating beyond that point.

Figure 6:
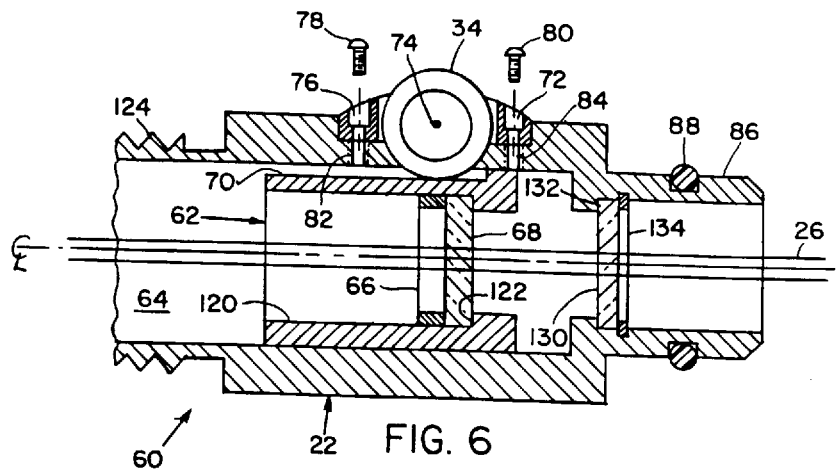
FIG. 6 is an enlarged detailed cross-sectional view of the focusing mechanism shown in FIG. 4.
Figure 7:
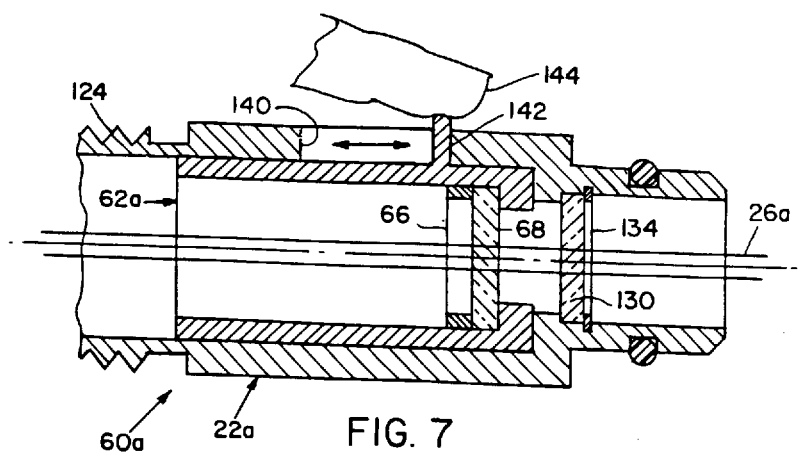
FIG. 7 is an enlarged detailed view similar to FIG. 6 showing an alternative focusing mechanism according to this invention.

The focusing mechanism is shown in greater detail in FIG. 6, where it can be seen that wheel 34, easily rotated by one finger, frictionally engages friction surface 70 to drive inner zoom barrel 62 to and fro axially within chamber 64 of barrel 22. Inner zoom barrel 62 also includes an inner bore 120 in which is located lens 68 held in place against shoulder 122 by retainer ring 166. Threads 124 engage with nut 24, FIG. 2, for coupling of handpiece 20 to the end of articulated arm 18. A second lens 130 may be secured within chamber 64 against shoulder 132 in nipple 86 where it is held by lens retainer 134, which may be a snap ring, for example. In this embodiment the single handed focus adjustment is shown as a cooperating wheel and friction surface but this is not a necessary limitation of the invention. For example, rack and pinion gear assembly could be used, or a ball could be used in place of the wheel or an alternative focusing mechanism 60a, FIG. 7, may include a slot 140 in outer barrel 22a through which extends a tab 142 from inner zoom barrel 62. Thus by simply placing finger pressure such as by finger 144 and sliding tab 142 back and forth, lens 68 may be moved to and fro to adjust the focus of laser beam 26a. In addition, the motions need not be strictly axial; they could as well be helical, for example.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A surgical laser handpiece comprising:

an outer barrel having a longitudinal axis and an inner chamber said outer barrel connected to a surgical laser device providing a laser beam;

an inner zoom barrel movable in the chamber relative to the outer barrel;

at least a first lens device in the zoom barrel for propagating and focusing a laser beam;

an opening in the outer barrel;

a drive member disposed through the opening and externally accessible on the outer barrel, the drive member engaging the inner zoom barrel for moving the inner zoom barrel and said first lens device with one hand in the direction of the longitudinal axis of the outer barrel thereby varying the focus of the laser beam.

2. The surgical laser handpiece of claim 1 in which there is a second lens device mounted in the outer barrel optically aligned with the first lens device.

3. The surgical laser handpiece of claim 1 in which the drive member includes a rotatable wheel and the inner zoom barrel includes a friction drive surface which is engaged by the wheel to move the inner zoom barrel as the rotatable wheel is rotated.

4. The surgical laser handpiece of claim 1 in which the drive member includes a tab attached to the inner zoom barrel and extending through the outer barrel through the opening in the outer barrel.

* * * * *